United States Patent [19]

Neuenschwander et al.

[11] Patent Number: 4,892,884
[45] Date of Patent: * Jan. 9, 1990

[54] NOVEL HMG-COA REDUCTASE INHIBITORS

[75] Inventors: Kent W. Neuenschwander, Ambler; Anthony C. Scotese, King of Prussia, both of Pa.

[73] Assignee: Rorer Pharmaceutical Corporation, Fort Washington, Pa.

[*] Notice: The portion of the term of this patent subsequent to Sep. 5, 2006 has been disclaimed.

[21] Appl. No.: 279,898

[22] Filed: Dec. 5, 1988

Related U.S. Application Data

[63] Continuation-in-part of Ser. No. 135,805, Dec. 21, 1987, Pat. No. 4,863,957.

[51] Int. Cl.$^4$ ............................................. C07D 309/30
[52] U.S. Cl. ..................................... 514/460; 549/292; 514/570
[58] Field of Search .................. 549/292, 570; 514/460

[56] References Cited

U.S. PATENT DOCUMENTS

| | | | |
|---|---|---|---|
| 4,567,289 | 1/1986 | Willard | 560/59 |
| 4,611,067 | 9/1986 | Volante | 549/292 |
| 4,668,699 | 5/1987 | Hoffman et al. | 514/460 |
| 4,681,893 | 7/1987 | Roth | 514/422 |

Primary Examiner—Asok Pal
Attorney, Agent, or Firm—Imre (Jim) Balogh; James A. Nicholson

[57] ABSTRACT

Disclosed are novel 3-hydroxy-3-methylglutaryl-coenzyme A reductase inhibitors useful as antihypercholesterolemic agents represented by the formula

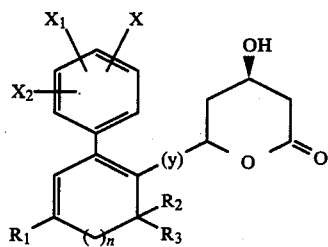

and the corresponding ring-opened hydroxy acids derived therefrom and pharmaceutically acceptable salts thereof.

Pharmaceutical compositions containing said compounds and method of inhibiting the biosynthesis of cholesterol therewith are also disclosed.

19 Claims, No Drawings

NOVEL HMG-COA REDUCTASE INHIBITORS

This application is a continuation-in-part application of U.S. Pat. application Ser. No. 135,805, filed Dec. 21, 1987, now U.S. Pat. No. 4,863957.

BACKGROUND OF THE INVENTION

1. Field of the Invention

The present invention relates to compounds, pharmaceutical compositions and a method useful for reducing serum cholesterol in humans. More particularly, the invention relates to trans-6-[(2-aryl substituted cycloalkadienyl) alkenyl or alkyl]-3,4,5,6-tetrahydro-4-hydroxy-2H-pyran-2-ones, the corresponding ring opened hydroxy acids derived therefrom and pharmaceutically acceptable salts thereof which are potent inhibitors of the enzyme 3-hydroxy-3-methylglutaryl-coenzyme A reductase (hereinafter HMG-CoA reductase), pharmaceutical compositions thereof, and a method of inhibiting biosynthesis of cholesterol for the treatment of atherosclerosis, hyperlipidemia and hypercholesterolemia.

2. Related Prior Art

Inhibitors of HMG-CoA are effective in lowering blood plasma cholesterol level as well as inhibiting the biosynthesis of cholesterol in humans. As such, inhibitors of HMG-CoA are useful in the prevention and treatment of coronary heart diseases. The prior art recognizes the importance of such compounds, e.g., Bethridge et al., Brit. Med. J., 4,500 (1975) and Brown et al., Scientific American, 58 Nov. (1984). Illustrative references directed to such compounds follow.

U.S. Pat. No. 4,681,893 to B. D. Roth pertains to trans-6-[2-(3-or 4-carboxamido-substituted pyrrol-1-yl)alkyl]-4-hydroxypyran-2-ones useful as hypochloesterolemic agents.

U.S. Pat. No. 4,668,699 to Hoffman et al. discloses semi-synthetic analogs of compactin and mevinolin and the dihydro and tetrahydro analogs thereof for antihypercholesterolemic application.

U.S. Pat. No. 4,282,155 to Smith et al. is directed to 6(R)-[2-(8'-Etherified-hydroxy-2',6'-dimethylpolyhydronaphtyl-1')ethyl]-4(R)-hydroxy-3,4,5,6-tetrahydro-2H-pyran-2-ones for inhibition of biosynthesis of cholesterol.

U.S. Pat. No. 4,567,289 relates to methyl, ethyl, n-propyl, 2-(acetylamino)ethyl, or 1-(2,3-dihydroxy)propyl ester of E-(3R,5S)-7-(4'-fluoro-3,3',5-trimethyl[1,1'-biphenyl]-2-yl)-3,5-dihydroxy-6-heptenoic acid that are HMG-CoA reductase inhibitors.

U.S. Pat. No. 4,611,067 discloses a process for the preparation of HMG-CoA reductase inhibitors which contain a 4-hydroxy-3,4,5,6-tetrahydro-2H-pyran-2-one moiety.

SUMMARY OF THE INVENTION

In accordance with the present invention, certain trans-6-[(2-aryl substituted cycloalkadienyl) alkenyl or alkyl]-3,4,5,6-tetrahydro-4-hydroxy-2H-pyran-2-ones and the corresponding ring-opened hydroxy-acids derived therefrom and pharmaceutically acceptable salts thereof are provided which are potent inhibitors of HMG CoA reductase. Specifically, the invention provides compounds of formula I.

and pharmaceutically acceptable salts thereof wherein:

Y is: —CHR—, —CHRCHR—, —CHRCHRCHR—, or —RC=CR—, wherein R is H or lower alkyl;

X, $X_1$ and $X_2$ are independently: H, F, Cl, Br, OH, $CF_3$ alkyl, or alkoxy;

$R_1$, $R_2$ and $R_3$ are independently: H, alkyl, $CF_3$, or aryl; and n=0 or 1

DETAILED DESCRIPTION OF THE INVENTION

As employed above and throughout the specification, the following terms, unless otherwise indicated, shall be understood to have the following meaning:

"Lower alkyl" means a saturated or unsaturated aliphatic hydrocarbon which may be either straight—or branched-chained containing from 1 to 4 carbon atoms.

"Alkyl" means a saturated or unsaturated aliphatic hydrocarbon which may be either straight-or branched-chained containing from about one to about six carbon atoms.

"Alkoxy" means an alkyl oxy group in which "alkyl" is as previously defined. Lower alkoxy groups are preferred which include methoxy, ethoxy, n-propoxy, i-propoxy, sec-propoxy, and n-butoxy.

"Aryl" means an aromatic hydrocarbon radical having 6 to 10 carbon atoms. The preferred aryl groups are phenyl, substituted phenyl and naphthyl. The term "substituted" means "alkyl" and halogen substitution.

The pharmaceutically acceptable salts of the present invention include those formed from sodium, potassium, calcium, aluminum, lithium, magnesium, zinc, lysine, arginine, procaine, ethylenediamine and piperazine.

The invention encompasses optical and stereoisomers of the compounds and mixtures thereof defined by the structural formula.

The general procedure for producing the compounds of the present invention is as follows:

Reaction Sequence

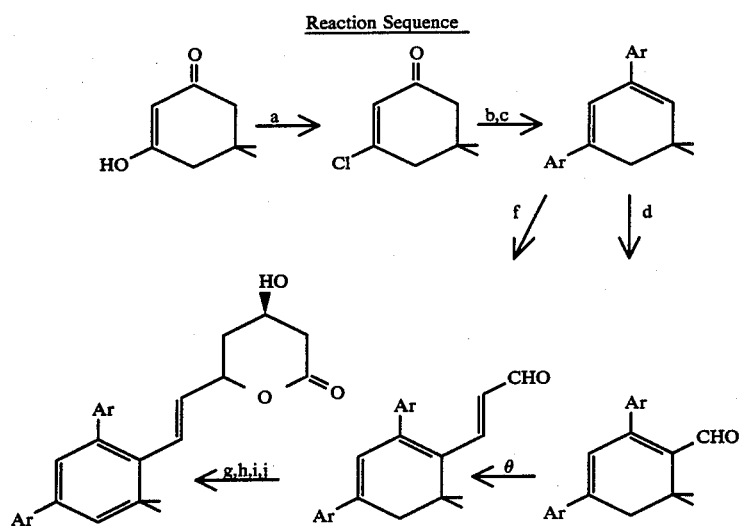

wherein the symbols used in the reactions denote the following reagents:

(a)(COCl)$_2$ (b)ArMgBr, CuI (c)PTSA (d)DMF, POCl$_3$

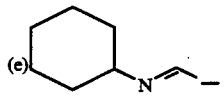

(f)Me$_2$NCHCHCHO, POCl$_3$ (g)$\overline{\text{CH}_2\text{COCHCO}_2\text{CH}_3}$ (h)Et$_3$B, NaBH$_4$ (i)NaOH, EtOH (j)DCC The starting materials were obtained from the Aldrich Chemical Co.; however, they may also be synthesized in accordance with methods known in the art.

The following preparative example will further illustrate the invention.

EXAMPLE 1

Step 1

Preparation of 3-chloro-5,5-dimethylcyclohex-2-en-1-one

The title compound was prepared using the method of Clark and Heathcock. *J. Org. Chem.*, 1976, 41, 636. To a suspension of dimedone (15.0 g, 107 mmol) in chloroform (40 ml) was added slowly oxalyl chloride (27.2 g, 214 mmol). The addition was accompanied by vigorous evolution of gas. After stirring at room temperature for 10 minutes, the slurry was refluxed for 20 minutes to give a yellow solution which was evaporated and distilled to give 15.7 g (92%) of chloroenone as a colorless liquid, bp 72° (5 mm).

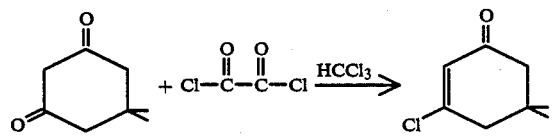

Step 2

Preparation of 1,3-di(4-fluorophenyl)-5,5-dimethylcyclohexa-1,3-diene

A Grignard reagent, freshly prepared from 1-bromo-4-fluorobenzene (27.47 ml, 250 mmoles) and magnesium powder (7.29 g, 300 mmoles) in 250 ml of THF was added dropwise, under nitrogen, to an ice cold mixture of copper iodide (1.90 g, 10 mmoles), 3-chloro-5,5-dimethylcyclohex-2-en-1-one (15.85 g, 100 mmoles) and 250 ml of THF. The reaction was warmed to room temperature and stirred overnight.

The dark reaction mixture was poured into a mixture of ice and 1 N HCl and extracted with ether. The ether layer was extracted with water and brine and the ether removed in vacuo.

The residue was redissolved in 250 ml toluene and treated with 1.90 g (10 mmoles) of p-toluenesulfonic acid. The toluene was refluxed for 1 hour in a Dean-Stark apparatus. The toluene was evaporated in vacuo and the residue chromatographed on silica gel with hexane as the eluent. Overall yield 19.52 g (66 mmoles).

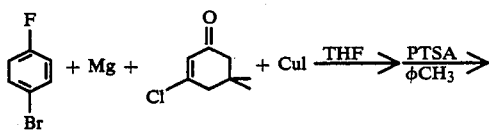

Step 3

Preparation of 2,4-di(4-fluorophenyl)-6,6-dimethylcyclohexa-1,3-dien-1-vl carboxaldehyde POCl$_3$ (4.66 ml, 50 mmoles) was added dropwise to an ice cold solution of 1,3-di(4-fluorophenyl)-5,5-dimethylcyclohexa-1,3-diene (14.8 g, 50 mmoles) and dimethylformamide (15.49 ml, 200 mmoles). The reaction was heated to 90° C. for 15 minutes, then cooled to 0° C.

The ice cold reaction was quenched by the dropwise addition of a solution of sodium acetate (27.22 g, 200 mmoles in 75 ml H$_2$O).

After stirring overnight, the reaction was diluted with ether and the layers separated. The ether layer was extracted with water, saturated sodium bicarbonate and brine. The ether was evaporated in vacuo and the residue chromatographed on silica gel. The product from the chromatography was crystallized from cold hexane to yield the aldehyde as yellow crystals.

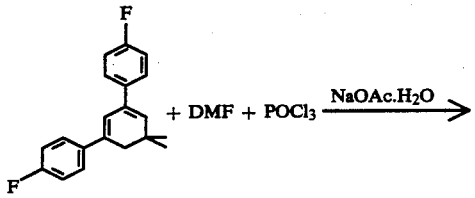

Step 4

Preparation of (E)-3-[2,4-di-(4-fluorophenyl)-6,6-dimethylcyclohexa-1,3-dien-1-yl]-2-propenaldehyde To a stirred solution of diisopropylamine (5.04 ml, 36 mmoles), in 72 ml of THF, at −60° C., under nitrogen, was added 13.2 ml, 33 mmoles of a 2.5M hexane solution of n-butyllithium. After 15 minutes, when the temperature had warmed to −40° C., a 1.0M THF solution of ethylidenecyclohexylamine (3.75 g, 30 mmoles) was added dropwise. The reaction was stirred for 30 minutes, while the temperature rose to −10° C. After stirring at −10° C. for an additional 10 minutes, the dark orange solution was cooled to −70° C. A 1.0M THF solution of the unsaturated aldehyde prepared in Step 3 (6.48 g, 20 mmoles) was added dropwise. The reaction was allowed to slowly warm to −10° C. and stirred for an additional hour.

The reaction was poured into H₂O and extracted with ether. The organic layer was extracted with brine and the solvents evaporated in vacuo.

The crude intermediate was chromatographed on silica gel with hexane and finally hexane/ethyl acetate (20/1) as eluents. The intermediate 3-hydroxy-propylidenecyclohexylamine was hydrolized on the silica gel column to the 2,4,6-trienal.

Steps 3 and 4 may be replaced with the alternative method described in Step 5.

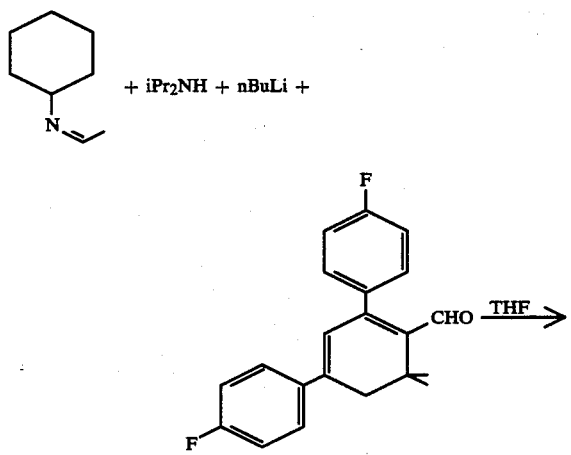

Step 5:

Preparation of (E)-3-[2,4-di-(4-fluorophenyl)-6,6-dimethylcyclohexa-1,3-dien-1-yl]2-propenaldehyde A 2.0M acetonitrile solution of 3-dimethylaminoacrolien (6.00 ml, 60 mmoles) was added dropwise to an ice cold 2.0M acetonitrile solution of POCl₃ (6.06 ml, 65 mmoles). After stirring for 15 minutes at 0° C., a 1.0M acetonitrile solution of the diene prepared in Step 2 (14.8 g, 50 mmoles) was added dropwise. When the addition was complete the reaction was heated to reflux for 4 hours.

After cooling to room temperature the reaction mixture was poured into 150 ml of ice cold 1N NaOH.

The aqueous layer was extracted with ether. The ether was removed in vacuo and the residue chromatographed on silica gel using hexane/ethyl acetate (20/1) as the eluent.

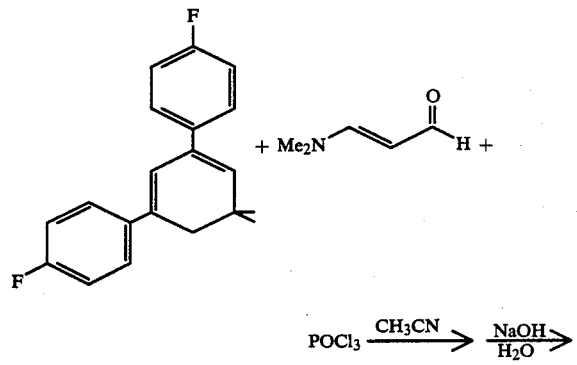

Step 6

Preparation of methyl-(E)-7-[2,4-di-(4-fluorophenyl-6,6-dimethylcyclohexa-1,3-dien-1-yl]-5-hydroxy-3-oxo-6-heptenoate To a stirred solution of diisopropyl amine (12.09 ml, 86.4 mmoles), in 173 ml of THF, at −60° C., under nitrogen, was added 31.68 ml (79.2 mmoles) of a 2.5M hexane solution of n-butyllithium. After 15 minutes, when the temperature had warmed to −40° C., methylacetoacetate (3.89 ml, 36 mmoles) was added dropwise. The solution was stirred for 30 minutes while the temperature was allowed to warm to −10° C.

To the yellow solution of the dianion was added a 0.25M THF solution of 10.50 g (30 mmoles) of the aldehyde prepared in Steps 4 or 5. The addition took 30 minutes. The reaction was stirred an additional 30 minutes at −10° C., then quenched with 9.47 ml (165.6 mmoles) of acetic acid in 40 ml of THF. The reaction was poured into ethyl acetate and extracted with H₂O, saturated NaHCO₃ and brine.

The residue was purified by flash chromatography on silica gel with hexane/ethyl acetate (5/1) as the eluent.

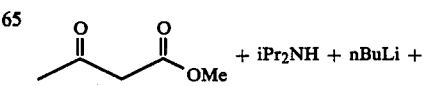

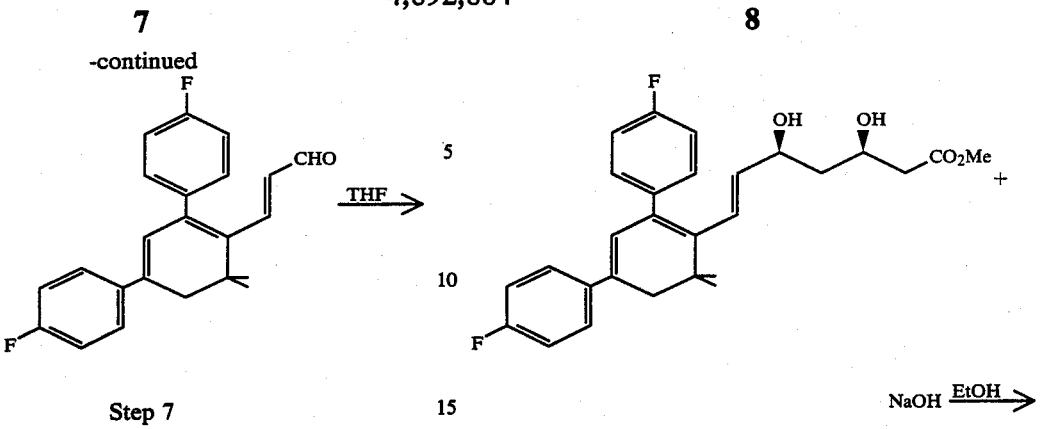

Step 7

Preparation of methyl-(E)-7-[2,4-di-(4-fluorophenyl)-6,6-dimethylcyclohexa-1,3-dien-1yl]-3,5-dihydroxy-6-heptenoate The 5-hydroxy-3-keto ester (11.18 g. 24 mmoles) prepared in Step 6 was dissolved in 60 ml of dry THF and treated with triethylborane (1M in THF, 36 ml, 36 mmoles). After aging for 5 minutes, at room temperature, the reaction mixture was cooled to −98° C. (MeOH-liquid $N_2$ bath). Sodium borohydride (1.04 g, 27.6 mmoles) was added, followed by dropwise addition of methanol (24 ml) over a 30 minute period. The reaction was stirred for 30 minutes at −98° C. and over the next 30 minutes was allowed to warm to −60° C. At −60 20 C. the reaction was quenched by the dropwise addition of 30% $H_2O_2$ (50 ML) in $H_2O$ (125 ml).

The reaction was warmed to room temperature and stirred for 30 minutes. It was poured into 1L of ethyl acetate and extracted with 620 ml of IN HCl. The organic layer was extracted with saturated $NaHCO_3$ and brine.

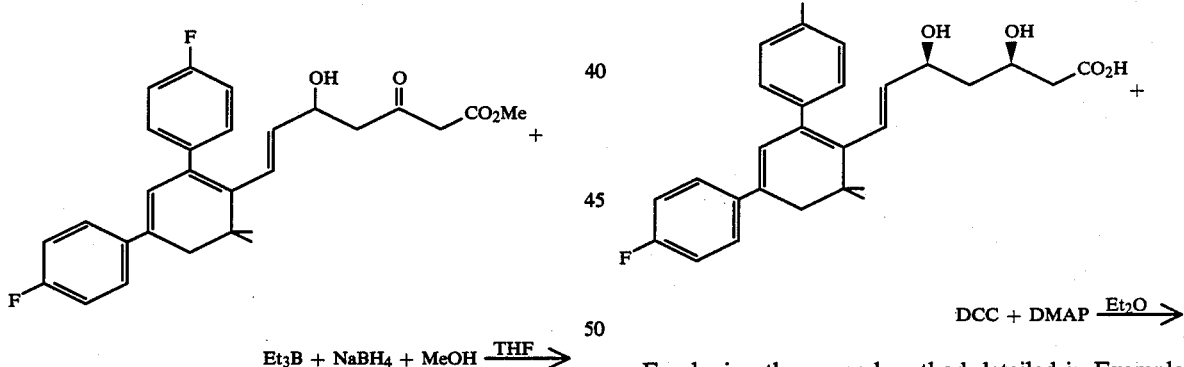

$Et_3B + NaBH_4 + MeOH \xrightarrow{THF}$

Step 8

Preparation of (E)-7-[2,4,-di-(4-fluorophenyl)-6,6-dimethylcyclohexa-1,3-dien-1-yl]-3,5,-dihydroxy-6-heptenoate Aqueous 1N NaOH (5 ml, 5 mmoles) was added to a 0.2M ethanol solution of the 3,5-dihydroxy ester prepared in Step 7 (1.87 g, 4 mmoles). After stirring for 10 minutes, the ethanol was evaporated in vacuo. The residue was redissolved in $H_2O$ and the aqueous layer was acidified with 1N HCl.

The aqueous layer was extracted with ether. The ether layer was extracted with brine and dried over $Na_2SO_4$. After filtration, the ether was removed in vacuo.

$\xrightarrow{NaOH \; EtOH}$

Step 9

Preparation of trans-(E)-6-[2-[2,4-di-(4-fluorophenyl)-6,6-dimethylcyclohexa-1,3-dien-1-yl]-ethenyl]-3,4,5,6-tetrahydro-4-hydroxy-2H-pyran-2-one Dicyclohexyl carbodiimide (0.91 g, 4.4 mmoles) and dimethylaminopyridine (0.049 g, 0.4 mmoles) were added to a 0.25M ether solution of the 3,5-dihydroxycarboxylic acid prepared in Step 8. After stirring for 4 hours at room temperature, the reaction was filtered. The residue was washed with ether and the combined filtrates evaporated in vacuo. The residue was chromatographed on silica gel and the product recrystallized from ether-hexane.

Anal. $C_{27}H_{26}F_2O_3$C 74.30, H 6.00.
Found C 74.18, H 6.03.

$\xrightarrow{DCC + DMAP \; Et_2O}$

Employing the general method detailed in Example 1, the following compounds can be prepared:

1. trans-(E)-6-[2-[2,4-di-(4-fluorophenyl)-6,6-dimethylcyclohexa-1,3-dien-1-yl]-ethenyl]-3,4,5,6-tetrahydro-4-hydroxy-2H-pyran-2-one;
2. trans-(E)-6-[2-[2,4-di-(3-methyl-4-fluoropheny)-6,6-dimethylcyclohexa-1,3-dien-1-yl]-ethenyl]-3,4,5,6-tetrahydro-4-hydroxy-2H-pyran-2-one;
3. erythro-(E)-7-[2,4-di-(3,4-dichlorophenyl)-6,6-dimethylcyclo hexa-1,3-dien-1-yl]-3,5-dihydroxy-6-heptenoic acid;
4. trans-6-[2-[2,4-di(3-chloro-4-fluorophenyl)-6,6-dimethylcyclohexa-1,3-dien-1-yl]-ethyl-3,4,5,6-tetrahydro-4-hydroxy-2H-pyran-2-one;
5. trans-(E)-6-[2-[2-(4-fluorophenyl)-4-phenyl-5,5-dimethylcyclopenta-1,3-dien-1-yl]-ethenyl]-3,4,5,6-tetrahydro-4-hydroxy-2H-pyran-2-one; and 6. erythro-(E)-7-[2-(4-fluoro-3-methylphenyl)-4-phenyl-5,5-dimethyl-1,3-dien-1-yl]-3,5-dihydroxy-6-heptenoic acid.

The compounds of the present invention are useful as hypocholesterolemic or hypolipidemic agents by virtue of their ability to inhibit the biosynthesis of cholesterol through inhibition of the enzyme HMG-CoA reductase. Having such ability, the compounds are incorporated into pharmaceutically acceptable carriers and administered to a patient in need of such cholesterol biosynthesis inhibition orally or parentally. Such pharmaceutical formulations to contain at least one compound according to the invention.

Suitable carriers include diluents or fillers, sterile aqueous media and various non-toxic organic solvents. The compositions may be formulated in the form of tablets, capsules, lozenges, trochees, hard candies, powders, aqueous suspensions, or solutions, injectable solutions, elixirs, syrups and the like and may contain one or more agents selected from the group including sweetening agents, flavoring agents, coloring agents and preserving agents, in order to provide a pharmaceutically acceptable preparation.

The particular carrier and the ratio of active compound to carrier are determined by the solubility and chemical properties of the compounds, the particular mode of administration and standard pharmaceutical practice. For example, excipients such as lactose, sodium citrate, calcium carbonate and dicalcium phosphate and various disintegrants such as starch, alginic acid and certain complex silicates, together with lubricating agents such as magnesium stearate, sodium lauryl sulphate and talc, can be used in producing tablets. For a capsule form, lactose and high molecular weight polyethylene glycols are among the preferred pharmaceutically acceptable carriers.

Where aqueous suspensions for oral use are formulated, the carrier can be emulsifying or suspending agents. Diluents such as ethanol, propylene glycol, and glycerin and their combinations can be employed as well as other materials.

For parenteral administration, solutions or suspensions of these compounds in aqueous alcoholic media or in sesame or peanut oil or aqueous solutions of the soluble pharmaceutically acceptable salves can be employed.

The dosage regimen in carrying out the methods of this invention is that which insures maximum therapeutic response until improvement is obtained and thereafter the minimum effective level which gives relief. Doses may vary, depending on the age, severity, body weight and other conditions of the patients but are ordinarily in the area of 5 mg/kg to 500 mg/kg of body weight in oral administration; such may, of course be given in two to four divided doses. With other forms of administration equivalent or adjusted doses will be administered depending on the route of administration.

The utility of the claimed compounds is measured by the test methods described hereunder. The methods are based on the articles: "Purification of 3-hydroxy-3-methylglutarylcoenzyme A reductase from rat liver" by Kleinsek et al., Proc. Natl. Acad. Sci. U.S.A., Vol. No. 4, pp. 1431–1435, April 1977 Biochemistry; "Mevinolin: A highly potent competitive inhibitor of hydroxy methyl glutaryl-coenzyme A reductase and a cholesterol-lowering agent" by Alberts et al., Proc. Natl. Acad. Sci. U.S.A., Vol 77, pp. 3951–3961, July 1980, Biochemistry; "Effects of ML-236B on cholesterol metabolism in mice rats: Lack of hypocholesterolemic activity in normal animals" by Endo et al., Biochimica et Biophysica Acta, 575 (1979) 266–276; and "Evidence of Regulation of 3-hydroxy-3-methylglutaryl coenzyme A reductase activity and cholesterol synthesis in nonhepatic tissues of rat" by Balasubramaniam et al., Proc. Natl. Acad. Sci. U.S.A., Vol. 73, No. 8, pp. 2564–2568, Aug. 1976, Biochemistry.

The first method used (designated HMGR Screen) was as follows. Male rats were acclimated to an alternate 12 hour light-dark cycle for a period of 2–3 weeks. The animals, weighing 180–230 g, were fed ad libitum a rat chow containing 2% cholestyramine for 5 days prior to sacrifice at the mid-dark period. Liver microsomes were prepared and HMGR enzyme was solubilized from the microsomes by freeze-thaw manipulation in high ionic strength buffer. The enzyme preparation was stored at $-80°$ C. in 300 $\mu$l portion samples. Prior to use, the enzyme was activated at 37° C. for 30 minutes in a reaction mixture. The reaction mixture contained in a volume of 240 $\mu$l : 0.14 M potassium phosphate buffer (pH 7.0); 0.18 M KCl; 3.5 mM EDTA; 10 mM dithiothreitol; 0.1 mg/ml BSA; 30,000 cpm of [$^{14}$C]HMG-CoA; 20 $\mu$M HMG-CoA, and 200 $\mu$g of solubilized enzyme with and without inhibitors (in 10 $\mu$l DMSO). After 5 minutes incubation at 37° C. the reaction was initiated with 0.2 mM NADPH. The final assay volume was 300 $\mu$l. The reaction then was terminated with 100 $\mu$l of 1N HCl. After an additional incubation for 15 minutes at 37° C. to allow for complete lactonization of the product, the mixture was diluted with 3 ml GDW. The diluted mixture was then poured over a $0.7 \times 1.4$ cm column containing 100–200 mesh Bio-Rex ion-exchange resin (cloride form of Bio-Rad) which was equilibrated with distilled water. With this resin the unreacted [$^{14}$C] HMG-CoA was adsorbed and the product 14C] lactone was eluted (80% recovery) directly into scintillation vials. After the addition of 10 ml of Aquasol ®, radioactivities of the samples were measured in a scintillation counter. Result on compound obtained in Example 1, Step 11 and compound obtained in Example 1, Step 12 is shown in Table I.

The second method used, designated Ex-Vivo Fasted, was as follows. Rats of 170–210 g were maintained on a low cholesterol diet for one week prior to use. Drugs (identified in Table I) were given orally in 0.5% methocel to fasted (fasted for 16 hours) rats. After one hour the rats were decapitated and their livers removed and transferred to chilled oxygenated Kreb's-Ringer-bicarbonate buffer (pH 7.4). The livers were then chopped into 0.5 mm slices using a McIlwain tissue chopper, and were suspended in the same buffer. Aliquots of the suspension containing 100 mg tissue were pipetted to culture tubes which contained [$^{14}$C] sodium acetate (2 $\mu$Ci, 1 mM). The tubes were gassed with 95% $O_2/5\%CO_2$, capped and incubated at 37° C. in a shaking water bath at 150 oscillation/min. for two hours. The final assay volume was 1.0 ml. After incubation the reaction was stopped by the addition of 1.0 ml of 15% KOH in ethanol, and the internal standard 3H-cholesterol was added. The tubes were recapped and the samples were saponified at 75° C. for two hours with periodic mixing. Subsequently an aliquot was removed for protein analysis using Bio-Rad's standard kit, and the remainder of the saponified samples was extracted with 10 ml of petroleum ether for 30 minutes. The lower aqueous phase was frozen in a dry ice/alcohol mixture and the ether layer was poured into labelled tubes. The ether was then evaporated to dryness and the cholesterol was separated by thin layer chromatography on plastic silica gel plates. After visualization with iodine the cholesterol spots were cut and counted with liquid scintillation fluid. Results on the following compounds and lactone form thereof, identified as A and B and A/L and B/L are shown in Table I.

(A.)

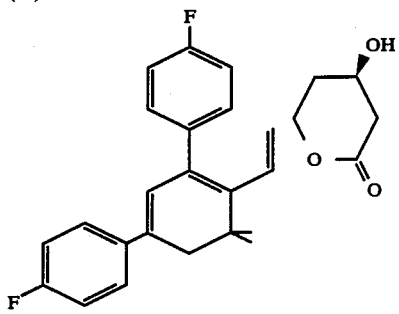

(B.)

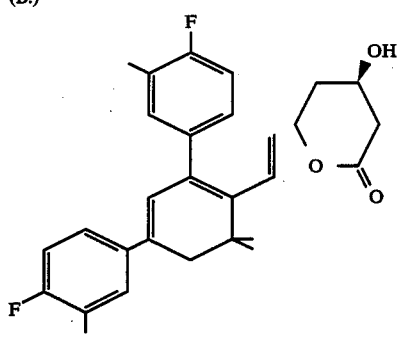

TABLE I

| Assay | Compound A | Compound A/L | Compound B | Compound B/L |
|---|---|---|---|---|
| *HMGR Screen | 5 μM | 0.33 μM | 50 μM | 0.84 μM |
| **Ex Vivo Fasted | 5 ± 19% | | 55 ± 6% | |

*IC$_{50}$ (Micromoles per liter)
**% Inhibition

*The micromolar concentration of compound required for 50% inhibition of cholesterol synthesis = IC$_{50}$
**% Inhibition at 1 mg/kg

What is claimed is:
1. A compound of the formula

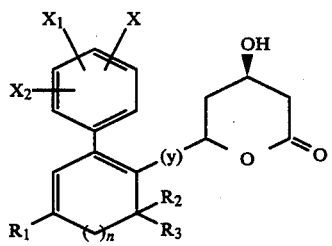

and pharmaceutically acceptable salts thereof wherein:
Y is: —CHR—,
—CHRCHR—,
—CHRCHRCHR—, or
—RC=CR—, wherein R is H or lower alkyl;

X, X$_1$ and X$_2$ are indepently: H, F, Cl, Br, OH, CF$_3$ alkyl, or alkoxy;

R$_1$, R$_2$ and R$_3$ are independently: H, alkyl, CF$_3$, aryl; haloaryl and n=0 or 1.

2. The compound of claim 1 wherein R is lower alkyl of 1 to 4 carbon atoms.

3. The compound of claim 1 wherein X, R$_1$, R$_2$ and R$_3$ are alkyl of 1 to 6 carbon atoms.

4. The compound of claim 1 wherein X is alkoxy of 1 to 6 carbon atoms.

5. The compound of claim 1 wherein at least one of the R$_1$, R$_2$ and R$_3$ radicals is phenyl.

6. The compound of claim 1 wherein at least one of the R$_1$, R$_2$ and R$_3$ radicals is substituted phenyl.

7. The compound of claim 1 wherein at least one of the R$_1$, R$_2$ and R$_3$ radicals is naphthyl.

8. The compound of claim 1 wherein X is F; R$_1$ is H; and R$_2$ and R$_3$ are —CH$_3$.

9. The compound of claim 1 wherein X is F; and R$_1$ is phenyl.

10. Trans-(E)-6-[2-[2,4-di-(4-fluorophenyl)-6,6-dimethylcyclohexa-1,3-dien-1-yl]-ethenyl]-3,4,5,6-tetrahydro-4-hydroxy-2H-pyran-2-one.

11. Trans-(E)-6-[2-[2,4-di-(3-methyl-4-fluorophenyl)-6,6-dimethylcyclohexa-1,3-dien-1-yl]-ethenyl]-3,4,5,6-tetrahydro-4-hydroxy-2H-pyran-2-one.

12. Erythro-(E)-7-[2,4-di-(3,4-dichlorophenyl)-6,6-dimethylcyclohexa-1,3-dien-1-yl]-3,5-dihydroxy-6-heptenoic acid.

13. Trans-6-[2-[2,4-di(3-chloro-4-fluorophenyl)-6,6-dimethylcyclohexa-1,3-dien-1-yl]-ethyl-3,4,5,6-tetrahydro-4-hydroxy-2H-pyran-2-one.

14. Trans-(E)-6-[2-[2-(4-fluorophenyl)-4-phenyl-5,5-dimethylcyclopenta-1,3-dien-1-yl]-ethenyl]-3,4,5,6-tetrahydro-4-hydroxy-2H-pyran-2-one.

15. Erythro-(E)-7-[2-(4-fluoro-3-methylphenyl)-4-phenyl-5,5-dimethyl-1,3-dien-1-yl]-3,5-dihydroxy-6-heptenoic acid.

16. A hypocholesterolemic, hypolipidemic pharmaceutical composition comprising a therapeutically effective amount of a compound of claim 1 and a pharmaceutically acceptable carrier.

17. The pharmaceutical composition of claim 16 wherein said compound is selected from the group consisting of:
trans-(E)-6-[2-[2,4-di-(4-fluorophenyl)-6,6-dimethylcyclohexa-1,3-dien-1-yl]-ethenyl]-3,4,5,6-tetrahydro-4-hydroxy-2H-pyran-2-one;
trans-(E)-6-[2-[2,4-di-(3-methyl-4-fluorophenyl)-6,6-dimethylcyclohexa-1,3-dien-1-yl]-ethenyl]-3,4,5,6-tetrahydro-4-hydroxy-2H-pyran-2-one; and
erythro-(E)-7-[2,4-di-(3,4-dichlorophenyl)-6,6-dimethylcyclohexa-1,3-dien-1-yl]-3,5-dihydroxy-6-heptenoic acid.

18. The pharmaceutical composition of claim 16 wherein said compound is selected from the group consisting of:

trans-6-[2-[2,4-di(3-chloro-4-fluorophenyl)-6,6-dimethylcyclohexa-1,3-dien-1-yl]-ethyl-3,4,5,6-tetrahydro-4-hydroxy-2H-pyran-2-one;

trans-(E)-6-[2-[2-(4-fluorophenyl)-4-phenyl-5,5-dimethylcyclopenta-1,3-dien-1-yl]-ethenyl]-3,4,5,6-tetrahydro-4-hydroxy-2H-pyran-2-one; and erythro-(E)-7-[2-(4-fluoro-3-methylphenyl)-4-phenyl-5,5-diethyl-1,3-dien-1-yl]-3,5-dihydroxy-6-heptenoic acid.

19. A method of inhibiting cholesterol biosynthesis in a patient in need of such treatment comprising administering to said patient a pharmaceutical composition defined in claim 16.

* * * * *